United States Patent [19]

Tepper et al.

[11] Patent Number: 5,524,624

[45] Date of Patent: Jun. 11, 1996

[54] APPARATUS AND METHOD FOR STIMULATING TISSUE GROWTH WITH ULTRASOUND

[75] Inventors: John C. Tepper, Carrollton; Ike C. Thacker, Galveston, both of Tex.

[73] Assignee: AMEI Technologies Inc., Wilmington, Del.

[21] Appl. No.: 239,401

[22] Filed: May 5, 1994

[51] Int. Cl.$^6$ .............................. A61B 17/56; A61B 8/00
[52] U.S. Cl. .................. 128/660.03; 128/662.03; 601/2; 607/50; 607/51
[58] Field of Search ............... 128/653.1, 660.01, 128/660.03, 662.03, 662.06; 601/2; 607/50, 51

[56] References Cited

U.S. PATENT DOCUMENTS

| | | | |
|---|---|---|---|
| D. 320,659 | 10/1991 | Johansson et al. | D24/155 |
| D. 353,889 | 12/1994 | Erickson et al. | D24/155 |
| 2,067,589 | 1/1937 | Antrim | 47/48.5 |
| 2,298,232 | 10/1942 | Remund | 47/48.5 |
| 3,055,372 | 9/1962 | Browner | 128/421 |
| 3,646,940 | 3/1972 | Timm et al. | 607/51 |
| 3,702,755 | 11/1972 | Palmer | 47/48.5 X |
| 3,745,995 | 7/1973 | Kraus | 128/82.1 |
| 3,783,880 | 1/1974 | Kraus | 128/82.1 |
| 3,842,841 | 10/1974 | Brighton et al. | 128/419 |
| 3,874,372 | 4/1975 | Le Bon | 128/24 A |
| 3,881,873 | 5/1975 | Klowden | 47/48.5 X |
| 3,890,953 | 6/1975 | Kraus et al. | 128/1.5 |
| 3,892,552 | 7/1975 | Gay, Jr. | 47/48.5 X |
| 3,914,900 | 10/1975 | Bigelow et al. | 47/48.5 X |
| 3,915,151 | 10/1975 | Kraus | 128/1.5 |
| 3,918,440 | 11/1975 | Kraus | 128/82.1 |
| 3,946,762 | 3/1976 | Green | 47/48.5 |
| 4,026,304 | 5/1977 | Levy | 128/419 |
| 4,105,017 | 8/1978 | Ryaby et al. | 128/1.5 |
| 4,216,548 | 8/1980 | Kraus | 31/1.91 |
| 4,232,679 | 11/1980 | Schulman | 128/419 |
| 4,237,895 | 12/1980 | Johnson | 128/419 PG |
| 4,313,438 | 2/1982 | Greatbatch | 128/207.21 |
| 4,314,554 | 2/1982 | Greatbatch | 128/207.21 |
| 4,333,469 | 6/1982 | Jeffcoat et al. | 128/419 |
| 4,344,250 | 8/1982 | Fahlstrom | 47/48.5 X |
| 4,414,979 | 11/1982 | Hirshorn et al. | 128/419 |
| 4,432,361 | 2/1984 | Christensen et al. | 128/419 |
| 4,459,988 | 7/1984 | Dugot | 128/419 |
| 4,461,300 | 7/1984 | Christensen | 128/419 F |
| 4,467,808 | 8/1984 | Brighton et al. | 128/419 F |
| 4,506,673 | 3/1985 | Bonnell | 128/419 |
| 4,506,674 | 3/1985 | Brighton et al. | 128/419 |
| 4,514,865 | 5/1985 | Harris | 24/155 X |
| 4,519,394 | 5/1985 | Black et al. | 128/419 F |
| 4,530,360 | 7/1985 | Duarte | 128/419 |
| 4,535,775 | 8/1985 | Brighton et al. | 128/419 F |
| 4,549,546 | 10/1985 | Kelly et al. | 128/419 F |
| 4,549,547 | 10/1985 | Brighton et al. | 128/419 |
| 4,550,370 | 10/1985 | Baker | 364/413 |
| 4,556,051 | 12/1985 | Maurer | 128/15 |
| 4,561,426 | 12/1985 | Stewart | 128/1.5 |
| 4,561,443 | 12/1985 | Hogrefe et al. | |
| 4,598,713 | 7/1986 | Hansjurgens et al. | 128/421 |
| 4,600,010 | 7/1986 | Dugot | 128/419 |
| 4,602,638 | 7/1986 | Adams | 128/419 F |
| 4,611,597 | 9/1986 | Kraus | 128/419 |
| 4,613,937 | 9/1986 | Batty, Jr. | 364/413 |
| 4,619,264 | 10/1986 | Singh | 128/419 F |
| 4,651,468 | 3/1987 | Martinez et al. | 47/48.5 X |
| 4,654,574 | 3/1987 | Thaler | 320/14 |
| 4,665,896 | 5/1987 | LaForge et al. | 129/1 D |
| 4,665,920 | 5/1987 | Campbell | 128/422 |
| 4,679,560 | 7/1987 | Galbraith | 128/419 R |
| 4,683,896 | 8/1987 | Herbst et al. | 128/785 |
| 4,781,591 | 11/1988 | Allen | 433/174 |
| 4,785,244 | 11/1988 | Jin et al. | 324/260 |
| 4,793,325 | 12/1988 | Cadossi et al. | 600/14 |
| 4,889,111 | 12/1989 | Ben-Dov | 128/419 |
| 4,905,671 | 3/1990 | Senge et al. | 128/419 |
| 4,944,299 | 7/1990 | Silvian | 128/419 PT |
| 4,974,114 | 11/1990 | Kammerer | 361/159 |
| 4,993,413 | 2/1991 | McLeod et al. | 128/419 |
| 5,000,178 | 3/1991 | Griffith | 128/419 |
| 5,014,699 | 5/1991 | Pollack et al. | 128/419 |
| 5,030,236 | 7/1991 | Dean | 623/16 |
| 5,038,780 | 8/1991 | Boetzkes | 128/419 |
| 5,056,518 | 10/1991 | Pethica et al. | 128/419 |
| 5,058,582 | 10/1991 | Thaler | 128/419 F |
| 5,088,488 | 2/1992 | Markowitz et al. | 128/419 PG |
| 5,103,806 | 4/1992 | McLeod et al. | 128/419 |
| 5,143,069 | 9/1992 | Kwon et al. | 128/660.06 |
| 5,154,172 | 10/1992 | Terry, Jr. et al. | 128/419 R |

| 5,191,880 | 3/1993 | McLeod et al. ............ 128/419 |
| 5,211,160 | 5/1993 | Talish et al. ............... 607/51 |
| 5,350,351 | 9/1994 | Saffer ....................... 607/51 |

FOREIGN PATENT DOCUMENTS

| 0561068 | 9/1993 | European Pat. Off. . |
| 1466730 | 6/1987 | U.S.S.R. . |
| 8302901 | 9/1983 | WIPO . |

OTHER PUBLICATIONS

Dohrmann, George J. and Rubin, Jonathan M., "Intraoperative Ultrasound Imaging of the Spinal cord: Syringomyelia, Cysts, and Tumors—A Preliminary Report", *Surgical Neurologist*, vol. 18, No. 6, Dec. 1982, pp. 395–399, Little, Brown, & Co., Boston, Massachusetts.

Saba, Joseph M., "Echo–Encephalography", *Medical Electronics*, Sep.–Oct. 1970, pp. 96–103.

"A Simple Three–Terminal IC Bandgap Reference" by A. Paul Brokaw, pp. 388–393, undated.

"The Alternate Treatment of Fracture Nounion–Electrical Stimulation to Induce Osteogenesis" Brochure by Zimmer–USA, 1979.

*Primary Examiner*—Krista M. Zele
*Attorney, Agent, or Firm*—Baker & Botts

[57] ABSTRACT

A device (10, 18) stimulates with an ultrasound the growth of a tissue or produces an image at a site within a patient. A housing (12, 20, 22) may be subcutaneously implanted within the patient such that the ultrasound is directed toward the site. A generator (52), disposed within the housing (12, 20, 22), produces a signal, which a transducer (56, 84, 144) converts into the ultrasound. The transducer (56, 84, 144) is partially disposed within the housing (12, 20, 22). The device (10, 18) may include an imaging circuit (80) for processing ultrasound echoes received by the transducer (56, 84, 144) to generate images of the tissue at the site. A remote control (102) may be used to control the device (10, 18) while it is implanted within the patient.

3 Claims, 4 Drawing Sheets

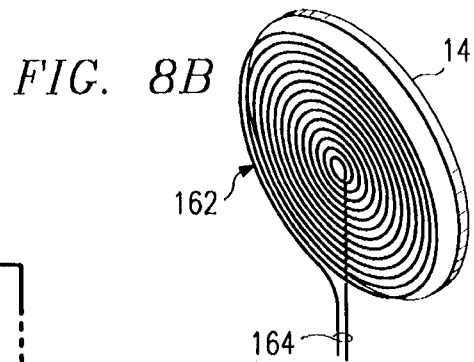
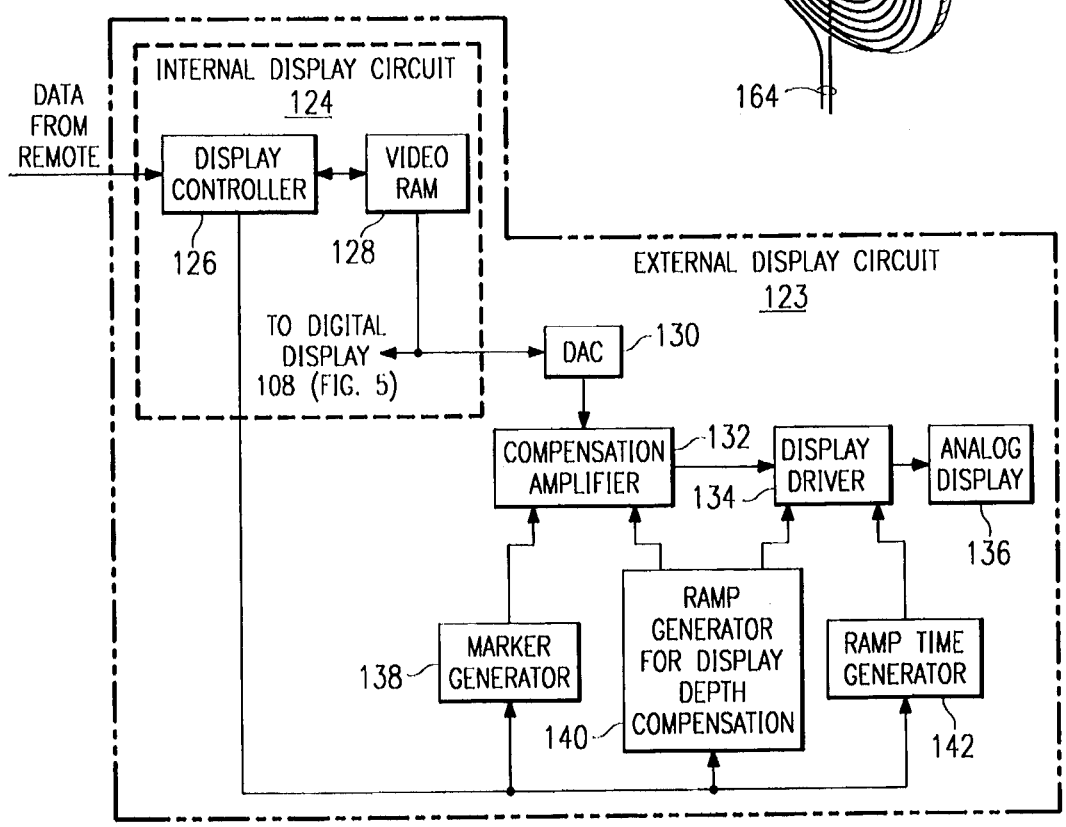
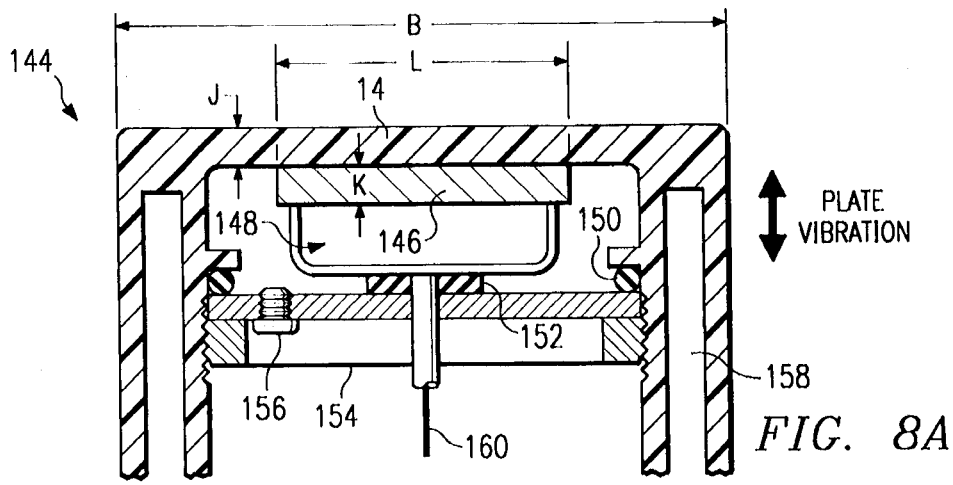

1

APPARATUS AND METHOD FOR STIMULATING TISSUE GROWTH WITH ULTRASOUND

CROSS-REFERENCE TO RELATED APPLICATIONS

This application is related to U.S. continuation-in-part application Ser. No. 08/018,944 filed Feb. 17, 1993, entitled "IMPLANTABLE TISSUE GROWTH STIMULATOR AND METHOD OF OPERATION". This application is also related to continuation application Ser. No. 08/186,230,, now U.S. Pat. No. 5,441,527, filed Jan. 24, 1994, entitled "IMPLANTABLE BONE GROWTH STIMULATOR AND METHOD OF OPERATION". This application is also related to U.S. Design application Ser. No. 29/004,938, now U.S. Pat. No. D361,555, filed Feb. 17, 1993, entitled "HAND-HELD PROGRAMMER/MONITOR". This application is also related to U.S. Design application Ser. No. 29/004,975, now U.S. Pat. No. D353,889, filed Feb. 17, 1993, entitled "IMPLANTABLE GROWTH STIMULATOR".

TECHNICAL FIELD OF THE INVENTION

The present invention relates generally to electronic devices and more specifically to devices for stimulating tissue growth and for imaging internal tissues with ultrasound.

BACKGROUND OF THE INVENTION

For the last quarter century, medical doctors have used ultrasonic sound waves, i.e., ultrasound, for generating images of sites within a patient's body. More recently, medical researchers have used ultrasound to promote the healing and growth of internal tissues such as bone. In both imaging and healing applications, a device applies the ultrasound either externally or invasively with respect to the patient, and directs the ultrasound toward the desired site.

An ultrasound imager processes ultrasound echoes to form images of internal tissues and organs. Ultrasound echoes are reflections of ultrasound from a first tissue at a boundary between the first tissue and a second tissue of a different density than the first. The imager calculates from the relative echo reception time and amplitude the relative position of a tissue boundary and the relative density of the reflecting tissue. An ultrasound growth stimulator causes ultrasonic vibrations in a tissue to promote the growth or healing thereof.

Ultrasound waveforms are characterized by their parameters, such as ultrasonic frequency, pulse amplitude, pulse width, and pulse repetition rate. These parameters may vary with the application. As an example of such parameters for imaging applications, "Diagnostic Ultrasound", Bruel & Kjaer, Marlborough, Mass. discloses an ultrasound frequency of 2–15 megahertz (MHZ), a pulse width of 1–5 microseconds (μs), and a pulse repetition rate of 1000 pulses per second (pps). As an example of such parameters for stimulation applications, U.S. Pat. No. 4,530,360, issued to Duarte, discloses an ultrasound frequency of 1.3–2 MHZ, a pulse width of 10–2,000 μs, and a pulse repetition rate of 100–1000 pps. Typically, an ultrasound stimulation pulse is stronger, i.e., has a larger amplitude, than an ultrasound imaging pulse.

Existing ultrasound imaging devices, such as the ones disclosed in "Echo-Encephalography", J. M. Saba, *Medical Electronics*, Issue 5, and "Intraoperative Ultrasound Imaging of the Spinal Cord", G. J. Dohrmann & J. McRubin, *Surgical Neurologist*, Vol. 18, No. 6, Dec. 1982 Little, Brown, & Co., Boston, Mass. have an external ultrasound transducer connected to a processing circuit and image display. As a trained operator holds the transducer against the patient's skin (which typically has been coated with an ultrasound coupling gel), a view is displayed of the internal tissues toward which the transducer is directing the ultrasound. The operator may move the transducer to display the desired view or multiple views.

It may be difficult for the operator to keep the transducer properly positioned, especially if the patient moves. Often, a patient must move a part of his body while the operator takes a series of images of the part. For example, a patient may have to slowly bend over as the operator takes a series of spine images that will show how the imaged area reacts to movement.

Also, the size and complexity of such an ultrasound imaging device typically force a patient to travel to the device's location (typically a medical center) for treatment. This traveling may be particularly burdensome when a doctor orders that a series of images be taken over an extended period. For example, a doctor may order that images be taken twice a week for two months so that he can monitor the healing of a tissue site, such as a bone fracture.

Existing ultrasound growth stimulators apply ultrasound to the treatment site either externally or invasively. Examples of external stimulators include U.S. Pat. Nos. 5,191,880 and 5,103,806, issued to McLeod et al., which disclose applying ultrasound to a bone site using vibrating floor plates and chairs, transducers attached to the skin, isometric exercises, or electrical muscle stimulation. U.S. Pat. No. 4,905,671, issued to Senge et al., discloses generating the ultrasound in and transmitting it to a bone site via a water bath in which is submersed the portion of the body containing the bone site. U.S. Pat. No. 4,530,360, issued to Duarte, discloses applying ultrasound to a bone site with a transducer held against the skin. Examples of invasive stimulators include U.S. Pat. No. 3,874,372, issued to Le Bon, which discloses a device having a needle that is inserted through the skin to apply ultrasound to an internal treatment site. U.S. Pat. No. 1,466,730, issued to Adarich, discloses two pins that are inserted into a bone on opposing sides of a fracture. The pins protrude through the skin and apply ultrasound directly to the bone site.

The design of external stimulators may hinder or prevent the patient or operator from keeping the ultrasound focused on the treatment site for the required time period, which may be several minutes or hours. For example, Duarte teaches a treatment having a preferred duration of 10–20 minutes, with some treatments lasting up to 55 minutes. It is often very difficult for the patient or operator to hold an ultrasound transducer in a fixed position, or for the patient to hold a portion of his body in a fixed position, for more than several minutes. Also, stimulators such as vibrating chairs or electrical muscle contractors are often unable to focus ultrasound, and thus may stimulate tissue sites not requiring or unable to withstand such stimulation.

Furthermore, external stimulators often must generate ultrasound waveforms of greater-than-required amplitude for promoting growth of the tissue site. External stimulators require additional power to generate this larger amplitude. Also, these stronger ultrasound waveforms may injure the intermediate tissue. The greater amplitude counterbalances the attenuation of the ultrasound caused by tissue intermediate to the ultrasound source and the tissue site.

Invasive stimulators require direct access to the treatment site via an opening in the patient's skin. This opening is prone to infection and may cause discomfort to the patient, particularly when the stimulator remains installed for an extended period of time. Additionally, the foreign presence in the patient's body may cause him further discomfort.

Like the above-discussed ultrasound imaging devices, the complexity of both external and internal stimulators often forces the patient to frequently make burdensome trips to a medical center for treatment. Typically, multiple applications of ultrasound are required over the course of treatment. For example, Duarte teaches daily treatments for 30–45 days. Also, a trained operator is usually needed to operate such stimulators. Additionally, the invasive devices often require a doctor to insert them into and remove them from the patient's body. The use of some invasive devices may even require the patient to remain in the hospital during the course of treatment.

SUMMARY OF THE INVENTION

In accordance with a first aspect of the present invention, an apparatus is provided for stimulating with ultrasound the growth of a tissue at a selected site within a patient. The apparatus includes a housing for subcutaneous implantation within the patient such that the ultrasound is directed toward the selected site. Disposed within the housing is a generator for producing a signal. Partially disposed within the housing is a transducer for converting the signal into the ultrasound.

In accordance with a second aspect of the present invention, an apparatus is provided for imaging with ultrasound a tissue at a selected site within a patient. The apparatus includes a housing for implantation within the patient such that the ultrasound is directed toward the selected site. Disposed within the housing is a generator for producing a signal. Partially disposed within the housing is a transducer for converting the signal into the ultrasound. In a related aspect of the invention, the apparatus has an array of such transducers, which increases the area that the apparatus can image.

In accordance with a third aspect of the present invention, an apparatus is provided for both stimulating and imaging with ultrasound a tissue at a selected site within a patient. The apparatus can operate in either a stimulating or imaging mode. The apparatus includes a housing for implantation within the patient such that the ultrasound is directed toward the selected site. Disposed within the housing is a generator for producing a signal and an imaging circuit for processing ultrasound echoes. Partially disposed within the housing is a transducer for converting the signal into the ultrasound. When the apparatus is in imaging mode, the transducer also receives ultrasound echoes and transforms them into electrical signals for processing by the imaging circuit. The apparatus may also include a memory for storing image data and a transmitter for transmitting the image data to a remote device. In a related aspect of the invention, the apparatus may include a plurality of such transducers. Each of these transducers may be used for stimulating a tissue, imaging a tissue, or both.

In a fourth aspect of the present invention, a remote device is provided that can control the operation of each of the above-mentioned apparatuses while it is implanted within the patient. The remote device includes a transmitter for sending instructions to an apparatus and a receiver for receiving data from an apparatus.

A first technical advantage provided by one aspect of the present invention is that it allows a patient to receive treatment without the presence of a trained operator.

A second technical advantage provided by another aspect of the present invention is that it allows a patient to receive treatment at a location other than a medical facility.

A third technical advantage of the invention provided by still another aspect of the invention is that it can accurately direct ultrasound for extended periods and while the patient is moving.

A fourth technical advantage provided by yet another aspect of the invention is that it does not require an opening in the patient's skin to internally apply ultrasound.

A fifth technical advantage provided by another aspect of the invention is that it can remain implanted within the patient's body throughout the course of treatment.

A sixth technical advantage provided by still another aspect of the present invention is that a single device can perform both stimulating and imaging functions.

A seventh technical advantage provided by yet another aspect of the present invention is that a user can control the operation of a stimulating or imaging device while it is implanted within the patient.

BRIEF DESCRIPTION OF THE DRAWINGS

For a more complete understanding of the present invention, and the advantages thereof, reference is now made to the following descriptions taken in conjunction with the accompanying drawings, in which:

FIG. 7 is a block diagram of a circuit for displaying image data generated by the stimulator-imagers of FIG. 1A and 1B;

FIG. 8A is a crystal-driven ultrasound transducer for use with the stimulator-imagers of FIGS. 1A and 1B; and FIG. 8B is a coil driving assembly, which is an alternative to the crystal driving assembly of the FIG. 8A ultrasound transducer.

DETAILED DESCRIPTION OF THE INVENTION

The illustrative embodiments of the present invention are best understood by referring to FIGS. 1–8B, wherein like numerals are used for like and corresponding parts of the various drawings.

Figure 1A:
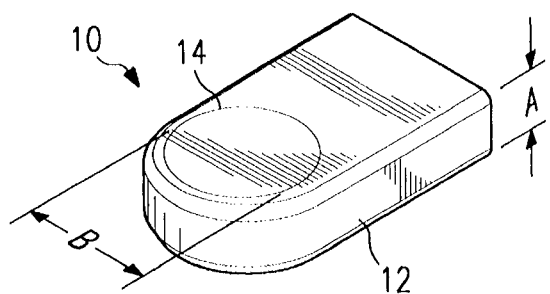
FIG. 1A is a subcutaneously implantable ultrasound stimulator-imager.

FIG. 1A shows a subcutaneously implantable ultrasound stimulator-imager 10 incorporating one embodiment of the present invention. As discussed below, stimulator-imager 10 includes circuitry that allows stimulator-imager 10 to perform ultrasound tissue-growth stimulation, imaging, or both stimulation and imaging.

Stimulator-imager 10 includes a housing 12 and a plate 14. Because stimulator-imager 10 is designed for implantation within the body of a patient (not shown), housing 12 and plate 14 may each be formed from surgical-grade stainless steel or titanium. Typically, thickness A of housing 12 is less than or approximately equal to 0.3", and diameter B of plate 14 is less than or approximately equal to 20 mm. As described below in conjunction with FIGS. 2A and 2B, plate 14 functions as a part of the vibrating portion of an ultrasound transducer 144 (FIG. 8A) that generates the ultrasound. In this embodiment, plate 14 may generate ultrasound waveforms for both stimulating and imaging applications. In other embodiments, housing 12 may be a cylinder having the same diameter as plate 14 and a height less than or approximately equal to 0.5".

Figure 1B:
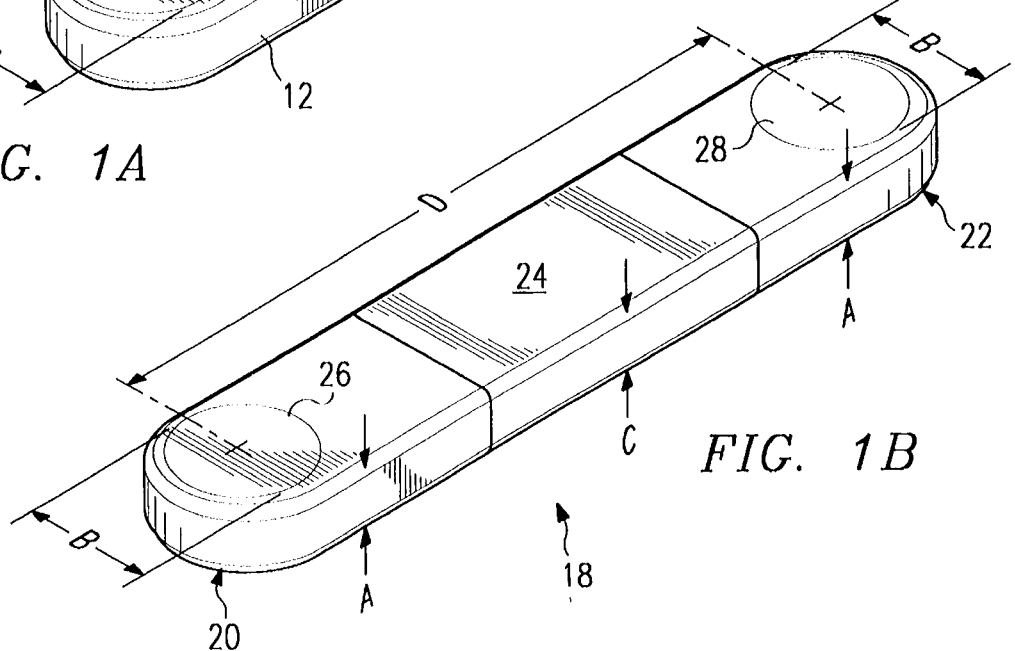
FIG. 1B is an alternate embodiment of the subcutaneously implantable stimulator-imager of FIG. 1A.

Stimulator-imager 18 is shown in FIG. 1B incorporating another embodiment of the present invention. Stimulator-imager 18 includes two housings 20 and 22 coupled with a flexible coupling member 24, and two plates 26 and 28. One of the plates 26 or 28 may generate ultrasound for tissue stimulating applications, and the other plate 26 or 28 may generate ultrasound for imaging applications.

Typically, housings 20 and 22 are similar to housing 12, and plates 26 and 28 are similar to plate 14. Coupling member 24 may be formed from silicone rubber or other biocompatible materials, and has a thickness C, which is approximately equal to thickness A. The length of coupling member 24 is such that the distance D between the centers of plates 26 and 28 is approximately 40–60 millimeters (mm). An important feature of the present invention is the ability to vary the spacing between plates 26 and 28 to optimize the stimulation and imaging for the specific tissue site and treatment therapy. For simplicity of discussion, only the operation of stimulator-imager 10 is hereinafter discussed, it being understood that stimulator-imager 18 operates in a similar fashion unless otherwise indicated.

In operation, a physician may subcutaneously implant stimulator-imager 10 within the patient's body so that plate 14 is approximately 40 mm from the tissue site (not shown) to be treated. For stimulator 18, the plate 26 or 28 used for imaging is preferably implanted approximately 40 mm from the tissue site. At this distance, the tissue site is beyond the near field relative to plate 14. The near field includes any distance from which an ultrasound echo will return to stimulator-imager 10 before the pulse giving rise to the echo has ended. Because the same transducer may be used to both generate the ultrasound and receive the echoes, these near-field echoes would be improperly processed; therefore, a tissue site within the near field would be improperly imaged. However, the physician may disregard this near-field consideration when plate 14 will only generate ultrasound for stimulating the tissue site.

Once stimulator-imager 10 is implanted, the physician may set the desired mode of operation with remote control device 102. Modes of operation and remote control device 102 are discussed below in conjunction with FIG. 5. At the end of treatment, the physician deactivates (with remote control device 102) and removes stimulator-imager 10 from the patient's body.

Both stimulator-imagers 10 and 18 are suited for promoting the fusion of two adjacent vertebrae and for generating images of the fusion site. In some applications, two or more stimulator-imagers 10 may be implanted for treatment of a tissue site. Some may be used for imaging, and others may be used for stimulating. This multiple implantation allows the stimulator-imagers 10 used for imaging to be implanted at a desired imaging distance, and the stimulator-imagers 10 used for stimulating to be implanted at a desired stimulating distance. Such multiple implantations of stimulator-imager 18 may also provide similar advantages.

An implantable device that stimulates tissue growth with an electric field is disclosed in U.S. Pat. No. 5,441,527, entitled "Implantable Bone Growth Stimulator and Method of Operation", filed 24 Jan. 1994 and assigned to the present assignee, which is a continuation of U.S. patent application Ser. No. 07/839,199, having the same title, filed 20 Feb. 1992, now abandoned. This patent application is hereby incorporated by reference herein.

Figure 2A:
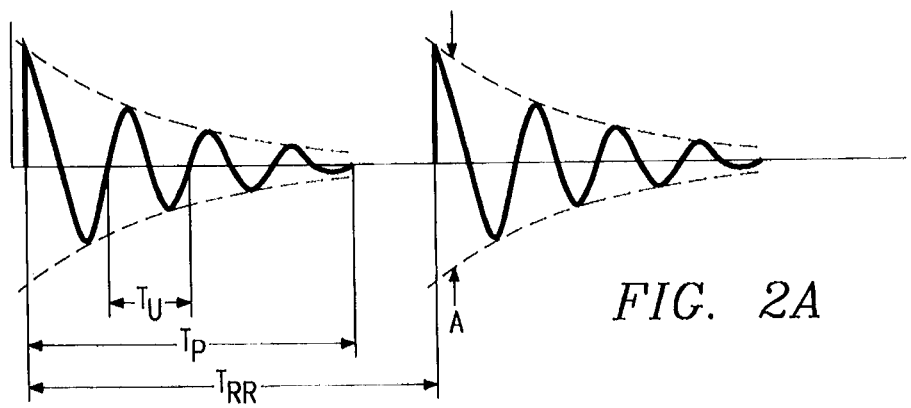
FIG. 2A is an ultrasound pulse for use in growth-stimulation applications.
Figure 2B:
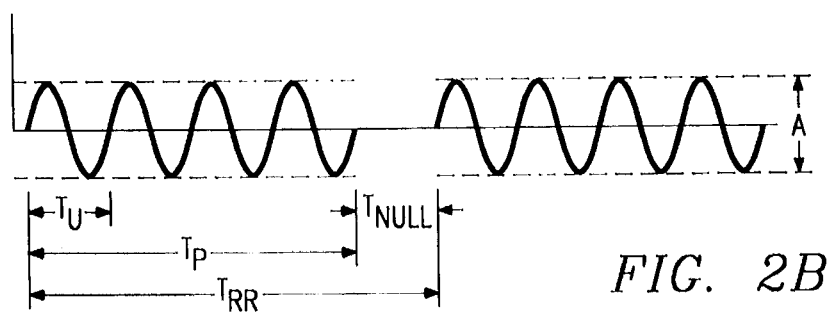
FIG. 2B is an ultrasound pulse for use in both imaging and growth-stimulation applications.

FIGS. 2A and 2B are examples of ultrasound waveforms that stimulator-imager 10 can generate. FIG. 2A represents a train of exponentially-decaying ultrasound pulses, i.e., shock waves, which are particularly useful to promote healing or stimulation of a tissue at a selected site. Shockwave parameters include the ultrasound period Tu, the pulse repetition period Trr, the pulse duration Tp, the ultrasound frequency fu=1/Tu, and the pulse repetition rate, i.e., pulse frequency, fp=1/Trr. To generate the shock wave, a short pulse of energy is applied to the ultrasound-producing medium of stimulator-imager 10. The decaying oscillations of the medium vibrate plate 14 to form the shock wave. As discussed below in conjunction with FIG. 8, the ultrasound-producing medium may be a piezoelectric crystal or a coil, and is designed to oscillate plate 14 at the desired frequency.

FIG. 2B is a train of ultrasound pulses for use in both imaging and healing or stimulation applications. Stimulator-imager 10 can vary the pulse-train parameters, which are described below, according to the application. 10 Typically, the ultrasound-producing medium is driven with ultrasound frequency fu for the pulse duration Tp. The medium is designed to both operate at the desired parameters and to minimize plate 14 oscillations after the driving signal is removed.

For imaging applications, ultrasound stimulator-imager 10 receives with its transducer the ultrasound echoes during the null between pulses, Tnull. Thus, Tnull should be long enough for stimulator-imager 10 to process the ultrasound echoes before the start of the next ultrasound pulse.

Figure 3:
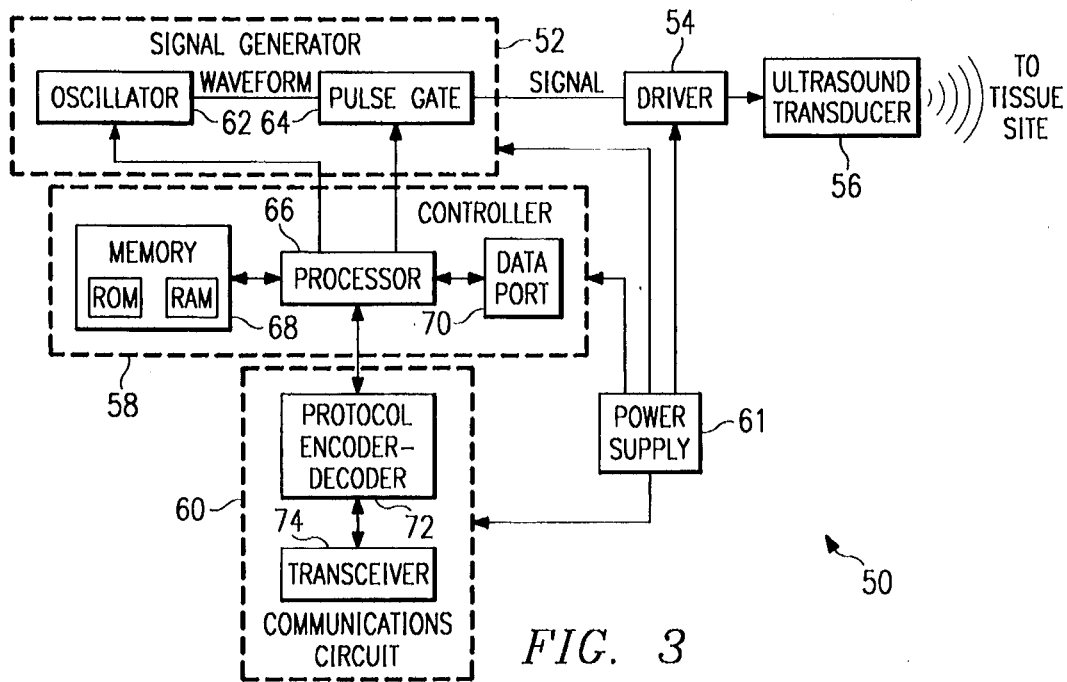
FIG. 3 is a block diagram of a stimulation circuit for the stimulator-imagers of FIG. 1A and 1B.

FIG. 3 is a block diagram of a stimulator circuit 50 for use with stimulator-imagers 10 and 18. Stimulator circuit 50 includes a signal generator 52 for generating an electrical signal. A driver 54 amplifies the signal, and with the amplified signal drives ultrasound transducer 56. Transducer 56 converts the electrical signal into ultrasound, and is discussed further in conjunction with FIG. 8A. Stimulator-imager 10 is preferably subcutaneously implanted in the patient's body such that transducer 56 (which includes plate 14) directs the ultrasound toward the desired treatment site. Controller 58 controls the functioning of generator 52. Communications circuit 60 provides a communication path between controller 58 and a remote device such as the programmer/monitor 102 of FIG. 5. A power supply 61, which is typically a battery, is included within stimulator-imager 10 to provide power to the components of stimulator circuit 50.

Signal generator 52 includes an oscillator 62 for generating, in response to controller 58, a desired waveform. Oscillator 62 can produce the waveform to have a desired waveshape, such as a sine wave, square wave, sawtooth wave, or exponentially decaying wave, desired parameters, such as frequency, duty cycle (if applicable), and amplitude, within predetermined ranges. Thus, controller 58 can tailor the waveform to the application.

Signal generator 52 also includes pulse gate 64 for producing, in response to controller 58, the electrical signal, which is the waveform in either continuous or pulsed form. Gate 64 acts as a switch, which when closed couples the waveform to driver 54. If controller 58 holds gate 64 closed, signal generator 52 provides a continuous signal. If controller 58 alternately opens and closes gate 64, signal generator 52 provides a pulsed signal where the pulse duration is the close time and the null between pulses is the open time. Thus, for a pulsed signal, controller 58 can control the durations of the pulses and the null therebetween.

Controller 58 includes a processor 66 executing a program for controlling oscillator 62 and pulse gate 64 as described above, and communications circuit 60 as described below. A memory 68 includes a non-volatile Read Only Memory (ROM) for storing the program, and may also include a Random Access Memory (RAM). A data port 70 allows loading of the program into memory 68 via processor 66 prior to-implantation of stimulator-imager 10.

Communications circuit 60 includes a protocol encoder-decoder 72 and a transceiver 74. Transceiver 74 receives down-link signals from remote device 102 (FIG. 5) and transmits up-link signals to the remote device. In accordance with a desired protocol, encoder-decoder 72 encodes data describing the status of stimulator-imager 10, i.e. stimulator-imager status data, from processor 66 into up-link signals and decodes operating instructions from down-link signals. A protocol that may be implemented by encoder-decoder 72 is described in U.S. Pat. No. 5,441,527, filed 24 Jan. 1994, which was previously incorporated by reference, and 08/018,944, entitled "Implantable Tissue Growth Stimulator and Method of Operation", filed on 17 Feb. 1993, and assigned to the present assignee, which is a continuation-in-part of U.S. application Ser. No. 07/839,199, now abandoned, and incorporated by reference herein.

The operation of circuit 50 is discussed for simplicity in conjunction with stimulator-imager 10, it being understood that the operation of circuit 50 is similar in conjunction with stimulator-imager 18 unless otherwise indicated. In operation, processor 66 receives operating instructions from the remote device via communications circuit 60, and controls stimulator circuit 50 in accordance therewith. Such instructions may include the mode of operation, the waveform shape and parameters, and the signal type (pulse or continuous), or may merely request stimulator-imager status data from processor 66.

One mode of operation may be a cycle where stimulator-imager 10 pulses a certain waveform for a first portion of the cycle and then produces no signal for a second portion of the cycle. Other modes of operation may put stimulator-imager 10 in an "on" or "off" state indefinitely. In response to a status request, processor 66 executes a status routine to derive status data, which may include the current mode of operation, the battery voltage level, or the identities of malfunctioning components of stimulator circuit 50. Examples of operational modes, status routines, and status circuitry appear in pending U.S. patent application Ser. No. 08/018,944, which was previously incorporated by reference.

Figure 4:
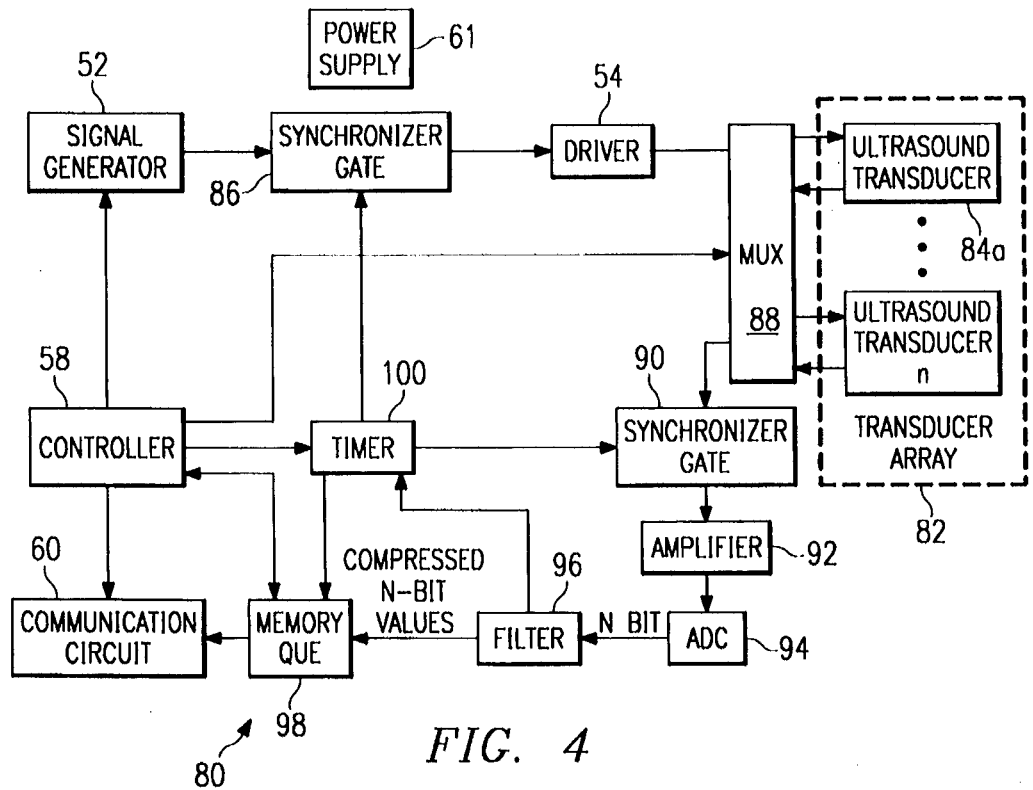
FIG. 4 is a block diagram of a stimulator-imager circuit for the stimulator-imagers of FIG. 1A and 1B.

FIG. 4 is a block diagram of a stimulator-imager circuit 80, which may be used with stimulator-imagers 10 and 18. Circuit 80 includes signal generator 52, driver 54, controller 58, communication circuit 60, and power supply 61 from stimulator circuit 50 of FIG. 3. 10 Replacing the single ultrasound transducer 56 of stimulator circuit 50 is an array 82 of ultrasound transducers 84*a–n*.

Figure 5:
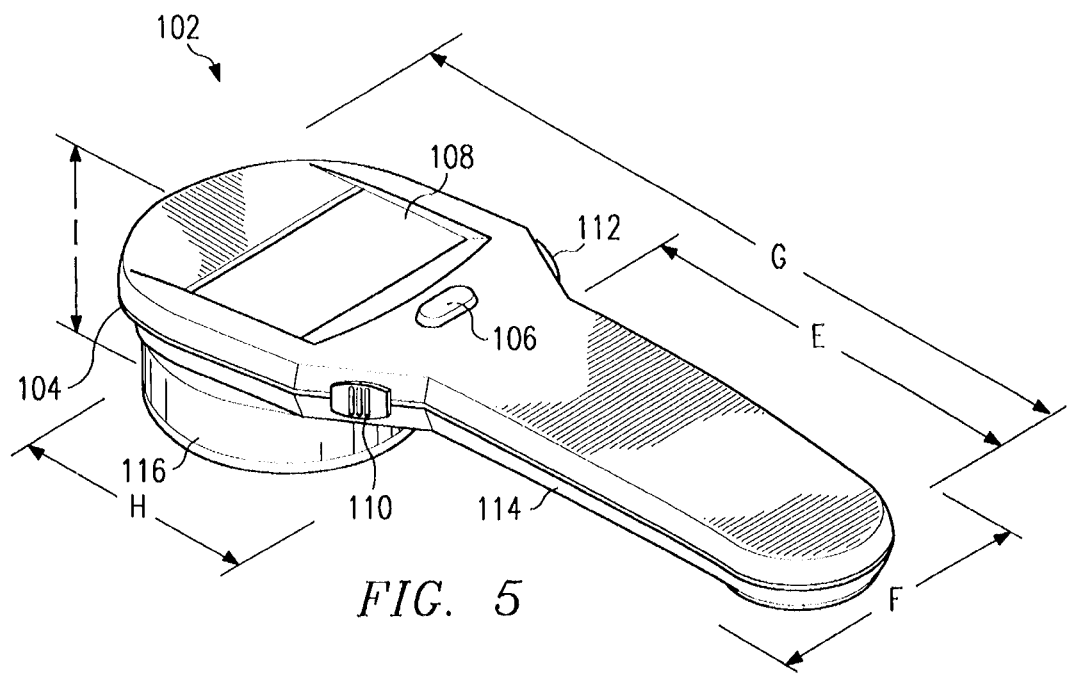
FIG. 5 is an elevational view of a remote control device for use with the stimulator-imagers of FIG. 1A and 1B.

A synchronizer gate 86 selectively couples the signal from signal generator 52 to driver 54. A multiplexer 88, responsive to controller 58, couples the signal from driver 54 to a selected ultrasound transducer 84. Multiplexer 88 also couples the echoes received from a selected ultrasound transducer 84 to a second synchronizer gate 90. Gate 90 couples the echoes to an amplifier 92, which amplifies the echoes and couples them to analog-to-digital converter (ADC) 94. ADC 94 converts the amplitudes of the echoes into a stream of n-bit values. In one embodiment of stimulator-imager circuit 80, n=16. ADC 94 couples the n-bit digital values to a filter 96. Filter 96 compresses and compensates the digital values and couples the compressed and compensated digital values to memory queue 98 for storage. In response to controller 58, memory queue 98 transfers the compressed and compensated n-bit digital values to communication circuit 60 for encoding and transmission to remote device 102 (FIG. 5). A timer 100, in response to instructions from controller 58, controls the operation of synchronizer gates 86 and 90. Timer 100 also receives data from filter 96, and in response thereto, controls and provides a time stamp to memory queue 98.

Stimulator-imager circuit 80 may operate in either a stimulating or imaging mode. The operation of circuit 80 in the stimulating mode is similar to the operation of stimulator circuit 50 of FIG. 3. Timer 100 holds synchronizer gate 86 closed to couple the signal from signal generator 52 to driver 54. Controller 58 instructs multiplexer 88 to select a desired one of the ultrasound transducers 84 for producing the ultrasound. Timer 100 holds synchronizer gate 90 open and disables memory queue 98 to inhibit the processing of echo pulses. Thus, while circuit 80 is operating in the stimulating mode, controller 58 disables the imaging function.

During the imaging mode, controller 58 instructs signal generator 52 to produce the desired imaging waveform in a manner similar to that described above in conjunction with FIG. 3 for the production of a stimulating waveform. Controller 58 also selects with multiplexer 88 the ultrasound transducer 84 that will generate the ultrasound. Timer 100 then commences ultrasound generation by closing synchronizer gate 86 to allow the signal to pass through driver 54 and mux 88 to the selected ultrasound transducer 84. Timer 100 also marks the time of this commencement and opens synchronizer gate 90 to inhibit echo processing while the transducer 84 is generating the ultrasound.

After the elapse of a predetermined time, timer 100 opens synchronizer gate 86 and continues to hold open synchronizer gate 90 for a second predetermined time. This holding open insures that any excess ultrasound generated by undamped oscillations of the transducer 84 after the opening of gate 86 is not mistakenly interpreted as an echo. After the second predetermined time has elapsed, timer 100 closes synchronizer gate 90 to enable the processing of echoes.

Typically, echoes are received with the same ultrasound transducer 84 that generated the ultrasound. That is, controller 58 instructs multiplexer 88 to receive the echoes from the same ultrasound transducer 84 to which multiplexer 88 originally coupled the signal. However, controller 58 may select one ultrasound transducer 84 to generate the ultrasound and another ultrasound transducer 84 to receive the echoes. The received echoes are coupled via multiplexer 88 and gate 90 to amplifier 92 and ADC 94, which amplify the echoes and convert them into n-bit digital values as described above.

Filter 96 performs compensation and compression algorithms on the n-bit digital values. The compensation algorithm compensates for the amplitude losses the ultrasound and echoes endure while passing through the tissue. Such losses, if left uncompensated, would corrupt the measurements of relative tissue densities. Echoes from a tissue boundary that is closer to transducer array 82 are attenuated less than echoes from a tissue boundary that is further away. Also, the denser a tissue through which the ultrasound and echoes must travel, the more the attenuation. Filter 96 compensates the echo amplitudes in proportion to the distance and tissue density through which the ultrasound and the echoes have traveled. Thus, these compensated amplitudes accurately reflect the relative densities of the tissues from whose boundaries they were reflected. For example, the compensated amplitudes of different bones' echoes would be substantially equal regardless of the distances between the bones and the transducer 84.

The primary function of the compression algorithm is to remove from the data stream extraneous data generated between consecutive echoes. Between echoes, the n-bit values will be approximately or equal to zero. These null values indicate that echoes with zero amplitude, i.e., no echoes, are being received. Because there may be relatively few tissue boundaries from which the echoes are generated, these null values may represent a large portion of the received data. Because only the echo amplitudes are used for imaging, these null values are extraneous. Filter 96 keeps these extraneous null values from needlessly occupying space in memory queue 98. Thus, only useful data is stored in memory queue 98. In an alternative embodiment, filter 96 may be disposed between amplifier 92 and ADC 94 as an analog filter without departing from the inventive concept.

Filter 96 signals timer 100 when it has echo-amplitude data to store in memory queue 98. Timer 100 provides a time stamp for each filtered n-bit value and then activates memory queue 98 to store the n-bit values and the associated time stamps. Each time stamp includes the elapse of time from the commencement of ultrasound generation to the time when the associated n-bit value is stored in memory queue 98, and the transducer 84 that produced the ultrasound and received the echo associated with the n-bit value. (When the echo data is processed, the relative times at which each echo is received and the identity of the producing-receiving transducer 84 provide the relative positions of the tissue boundaries with respect to this transducer 84.) Controller 58 then enables memory queue 98 to transmit these stored n-bit values, which represent echo amplitudes, and the associated time stamps to communication circuit 60, which transmits them to the remote device for processing.

The same operation may be repeated with the same or a different transducer 84. In this way, transducer array 82 allows imaging of a much greater tissue area than would a sole transducer 84. For example, controller 58 may begin with transducer 84a, and then successively repeat the imaging cycle for transducers 84b, 84c ... 84n. This will form an image of the tissues located in approximately a perpendicular direction from the plate of the producing-receiving transducer 84. Also, controller 58 can halt the generation of ultrasound when memory queue 98 becomes full, thus giving memory queue 98 a chance to transfer its contents to communication circuit 60 before it is overwritten with new data.

When circuit 80 is used with stimulator-imager 10, the single transducer represented by plate 14 generates ultrasound for either or both stimulating and imaging applications. With stimulator-imager 18, each transducer represented by plates 26 and 28 may be used to generate ultrasound for either or both imaging and stimulating applications. If both are used simultaneously for an imaging application, they will compose array 82.

Figure 6:
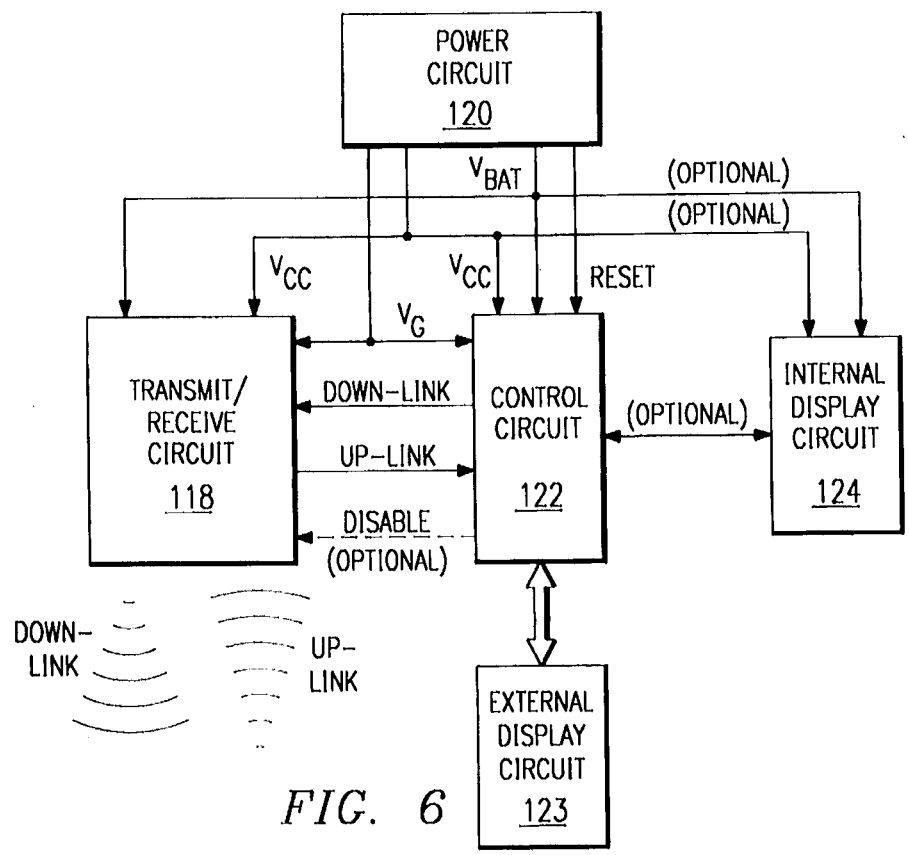
FIG. 6 is a block diagram of a circuit for the remote control device of FIG. 5.

FIG. 5 is an elevational view of a remote programmer/monitor or remote control device 102, which may be used with implantable stimulator-imager 10 (and 18) of FIG. 1A (and 1B). Remote device 102 includes a housing 104 for housing internal circuitry (FIG. 6). An on/off switch 106 selectively provides power to the internal circuitry. A display 108, typically a Liquid Crystal (LC) display, displays data received from stimulator-imager 10 or menus of instructions for transmission to stimulator-imager 10. Select buttons 110 and 112 allow a user to select an instruction from the displayed menu. A handle 114 is designed to facilitate one-handed operation of remote device 102. An antenna housing 116, which is part of housing 104, houses an antenna (not shown) for receiving and transmitting data from and to stimulator-imager 10.

FIG. 6 is a block diagram of the internal circuitry of remote device 102. The circuitry includes a transmit-receive circuit 118 for receiving uplink signals from and transmitting downlink signals to stimulator-imager 10. A power circuit 120, which typically includes a battery (not shown), provides voltages VCC, VG and VBAT to transmit-receive circuit 118 and a control circuit 122. Power circuit 120 also provides a power-up reset signal to control circuit 122. Control circuit 122 converts, i.e. encodes, selected instructions into downlinks for transmission to stimulator-imager 10 and converts, i.e. decodes, uplinks from stimulator-imager 10 into status data.

Control circuit 122 may be coupled via a port (not shown) to an external display circuit 123 for processing the image data from stimulator-imager 10 and displaying the ultrasound image. Alternatively, remote device 102 may include an internal display circuit 124 coupled to control circuit 122 for processing the image data to form the ultrasound image on display 108. Both external display circuit 123 and internal display circuit 124 are discussed further in conjunction with FIG. 7.

Control circuit 122 includes a processor (not shown) executing routines for displaying the instruction menus on display 108 and interpreting a user's choice of instructions to transmit to stimulator-imager 10. Control circuit 122 may also include self-diagnostic circuitry for testing transmit-receive circuit 118, power circuit 120, control circuit 122, and internal display circuit 124 (if installed) and for providing on display 108 the status of these circuits.

Embodiments of remote device 102, transmit-receive circuit 118, power circuit 120, and control circuit 122 and the operation thereof are further discussed in U.S. patent application Ser. No. 08/018,944, which was previously incorporated by reference.

In operation, a user holds remote device 102 over the portion of the patient's body in which stimulator-imager 10 is implanted. Preferably, antenna housing 116 is faced toward stimulator-imager 10 to optimize the communications channel between remote device 102 and stimulator-imager 10. The user moves switch 106 into the "on" position to active remote device 102. After remote device 102 performs its self-status check, and providing there are no detected malfunctions, the first instruction menu is displayed on display 108. The user selects the desired menu item with select buttons 110 and 112.

By selecting items from the menus, the user may set stimulator-imager 10 in any of the above-discussed operational modes. Also, the user can check the status of stimulator-imager 10 to insure it is functioning properly. Once the user is finished, he may remove remote control device 102 from its position over the body. Stimulator-imager 10 will function in the last mode set until instructed otherwise.

During an imaging mode, the user holds remote device 102 over the body portion containing stimulator-imager 10 to receive the imaging data from memory queue 98 via communications circuit 60 (FIG. 4). Remote device 102 may then store and process this data with internal display circuit 124, or couple the imaging data to external display circuit 123 for processing. Once the desired amount of imaging data has been received, the user instructs stimulator-imager 10 to exit the imaging mode and enter a stimulation or the "off" mode.

The operation of remote device 102 when used with stimulator-imager 18 is similar to that described above for stimulator-imager 102, with the addition that remote device 102 can control independently the operation of the two transducers represented by plates 26 and 28. For simplicity of discussion, the following advantages are presented with reference to stimulator-imager 10, it being understood that similar advantages are associated with stimulator-imager 18 unless otherwise indicated.

An advantage of stimulator-imager 10 is that the operational mode or sequence of modes can be set at the doctor's office so that stimulator-imager 10 will automatically perform the ultrasound applications over the course of treatment. For example, stimulator-imager 10 may be programmed to generate ultrasound for approximately 10 minutes each day at a specified time. Another advantage of the stimulator-imager 10/remote device 102 combination is that a patient may be trained to use remote device 102 to enter the desired stimulation mode or obtain image data. The image data may be coupled from remote 102 via a modem (not shown) to a remote display device for viewing by the doctor. Alternatively, the imaging data may be stored in memory queue 98 until the doctor retrieves it.

Thus, the above advantages allow the doctor to direct and monitor the healing process with a minimal number of patient office visits.

FIG. 7 is a block diagram of both external display circuit 123 and internal display circuit 124 of FIG. 6. Internal display circuit 124 includes a display controller 126, which receives image data from control circuit 122 and processes it for storage as digital video data in a Video Random Access Memory (VRAM) 128. The digital video data from VRAM 128 is displayed on digital display 108 (FIG. 5).

External display circuit 123 also includes a display controller 126 and VRAM 128. A digital-to-analog converter (DAC) 130 converts the digital video data stored in VRAM 128 into an analog video signal. Compensation amplifier 132 compensates and display driver 134 amplifies the analog video signal for display on analog display 136, which is typically a cathode ray tube (CRT). Marker generator 138, which is coupled between display controller 126 and compensation amplifier 132, generates markers on display 136. Ramp generator 140, which is coupled between display controller 126, and compensation amplifier 132 and display driver 134, generates a ramp to compensate the display depth of the image displayed on display 136. Ramp time generator 142 provides the horizontal and vertical sweeps for display 136.

In operation of both external display circuit 123 and internal display circuit 124, display controller 126 receives the image data, which comprises echo data with corresponding time stamps, from controller 122. Display controller 126 processes the echo data and time stamps, and stores the echo data in VRAM 128 for proper display timing. That is, display controller 126 uses the time stamps to store the corresponding echo data in appropriate VRAM 128 registers so that the tissue boundaries represented by the echoes are displayed in the correct vertical and horizontal positions. Typically, the right edge of the display represents the position of transducer array 82 (FIG. 4). Thus, the horizontal position of a display point represents a relative perpendicular distance from transducer array 82, and the vertical position represents the position along array 82 (i.e., the particular transducer 84) where the echo associated with the point was received. In this way, an accurate image of the tissues and their boundaries is displayed.

FIG. 8A is one embodiment of an ultrasound transducer 144, which may compose transducer 56 (FIG. 3) or transducers 84 (FIG. 4). Ultrasound transducer 144 includes plate 14 (FIG. 1A), a piezoelectric crystal 146 attached to the inner side of plate 14, a sealed air box 148, elastomeric seals 150 and 152, a bushing 154 with a fill screw 156, a cooling jacket 158, and an electrical feed wire 160. (Although the plate is referred to as plate 14, transducer 144 may also be used in conjunction with plates 26 and 28 of FIGURE 1B.) Plate 14 is electrically grounded via the walls of cooling jacket 158, and crystal 146 is coupled to wire 160 via the walls of air box 148.

The thickness J of plate 14 and the material from which crystal 146 is formed are chosen to provide a close acoustic impedance match between transducer 144 and the surrounding tissue. A close impedance match reduces or eliminates ultrasound reflections from the transducer/tissue boundary. Thickness J is preferably half the wavelength of the desired ultrasound, i.e., $\lambda/2$. (For example, for a 15 MHZ ultrasound, $\lambda=10$ mm and J=5 mm.) Piezoelectric crystal 146 is preferably formed from a polyvinylidene fluoride (PVDF) film. Such a crystal has an acoustic impedance near that of water, which composes a majority of the surrounding tissue. Thickness K and diameter L are selected such that crystal 146 vibrates at the desired frequency.

In operation, the vibration of plate 14 produces the ultrasound. A voltage is applied via wire 160 across piezoelectric crystal 146. This voltage forces crystal 146 to vibrate at the desired frequency and in the direction shown. Because plate 14 is attached to crystal 146, plate 14 also vibrates at the desired frequency and in the direction shown. Transducer 144 is useful for generating ultrasound waveforms as shown in FIGS. 2A and 2B. Thus, transducer 144 may be used for both imaging and stimulating applications.

FIG. 8B is an alternative embodiment of a plate-vibrating mechanism for ultrasound transducer 144. With joint reference to FIG. 8A, piezoelectric crystal 146 is replaced with a planar driving coil 162, which is rigidly mounted within air box 148 a distance from plate 14. Feed line 160 is replaced with a pair of feed lines 164.

In operation, pulses of current drive coil 162 via feed lines 164. These current pulses generate a magnetic field, which induces eddy currents in plate 14. These eddy currents generate an opposing magnetic field, which interacts with the original magnetic field. This interaction causes plate 14 to generate an ultrasound shock pulse as shown in FIG. 2A. Thus, an ultrasound transducer having planar coil 162 may be used for tissue stimulating applications.

Although the present invention and its advantages have been described in detail, it should be understood that various changes, substitutions and alterations can be made therein without departing from the spirit and scope of the invention as defined by the appended claims. For example, transducer 144 alone may be implanted within the patient's body, with the associated electronics remaining external to the patient.

What is claimed is:

1. An apparatus for using ultrasound to stimulate the growth of a tissue at a site within a patient and to generate an image of the site, the apparatus comprising:

a housing for implantation within the patient such that the ultrasound is directed toward the site;

a generator, disposed within said housing, for producing a signal;

a first transducer, partially disposed within said housing, for converting said signal into the ultrasound, for directing the ultrasound toward the site, and for receiving an ultrasound echo from the site; and a second transducer and wherein said generator generates a first and a second signal such that said first transducer is for converting said first signal into a first ultrasound for imaging the tissue and said second transducer is for converting said second signal into a second ultrasound for stimulating the tissue.

2. An apparatus for using ultrasound to stimulate the growth of a tissue at a site within a patient and to generate an image of the site, the apparatus comprising:

a housing for implantation within the patient such that the ultrasound is directed toward the site;

a generator, disposed within said housing, for producing a signal;

a first transducer, partially disposed within said housing, for converting said signal into the ultrasound, for directing the ultrasound toward the site, and for receiving an ultrasound echo from the site, wherein said first transducer receives a plurality of ultrasound echoes from the site;

an analog-to-digital converter for converting the echoes into digital values;

a first synchronizer for decoupling said analog-to-digital converter from said transducer when said transducer is converting said signal into ultrasound;

a second synchronizer for decoupling said generator from said transducer when said analog-to-digital converter is converting the echoes into said digital values;

a filter for filtering said digital values;

a timer for generating time stamps for said filtered digital values and for controlling said first and second synchronizers; and a memory for storing said filtered digital values and said time stamps.

3. A method for stimulating the growth of a tissue at a site within a body with ultrasound and generating an image of the site with said ultrasound, the method comprising the steps of:

subcutaneously implanting a housing having a generator and a transducer within said body approximately forty millimeters from said site and beyond the near field, such that said transducer directs said ultrasound toward said site;

producing an electrical signal with said generator having a waveform with parameters as desired for tissue growth stimulation and image generation; and transforming said signal into said ultrasound with said transducer.

* * * * *